United States Patent
Ante et al.

(10) Patent No.: US 9,976,980 B2
(45) Date of Patent: May 22, 2018

(54) SENSOR DEVICE

(71) Applicant: CONTINENTAL AUTOMOTIVE GMBH, Hannover (DE)

(72) Inventors: Johannes Ante, Regensburg (DE); Philippe Grass, Regensburg (DE)

(73) Assignee: Continental Automotive GmbH, Hannover (DE)

( * ) Notice: Subject to any disclaimer, the term of this patent is extended or adjusted under 35 U.S.C. 154(b) by 101 days.

(21) Appl. No.: 14/778,463

(22) PCT Filed: Mar. 19, 2014

(86) PCT No.: PCT/EP2014/055531
§ 371 (c)(1),
(2) Date: Sep. 18, 2015

(87) PCT Pub. No.: WO2014/147139
PCT Pub. Date: Sep. 25, 2014

(65) Prior Publication Data
US 2016/0290954 A1 Oct. 6, 2016

(30) Foreign Application Priority Data
Mar. 20, 2013 (DE) .................. 10 2013 204 911

(51) Int. Cl.
*G01N 27/407* (2006.01)
*G01M 15/10* (2006.01)
(52) U.S. Cl.
CPC ...... *G01N 27/4077* (2013.01); *G01M 15/104* (2013.01); *G01N 27/407* (2013.01); *G01N 27/4078* (2013.01)
(58) Field of Classification Search
CPC .............. G01M 15/104; G01N 27/407; G01N 27/4077; G01N 27/4078
See application file for complete search history.

(56) References Cited

U.S. PATENT DOCUMENTS

| 4,132,615 A | 1/1979 | Linder et al. |
| 5,505,073 A | 4/1996 | Gerblinger et al. |
| (Continued) | | |

FOREIGN PATENT DOCUMENTS

| DE | 43 24 659 C1 | 4/1995 |
| DE | 195 23 978 A1 | 1/1997 |
| (Continued) | | |

OTHER PUBLICATIONS

Office Action dated Dec. 1, 2016 which issued in the corresponding Chinese Patent Application No. 201480028973.4.

*Primary Examiner* — R. A. Smith
*Assistant Examiner* — John M Royston
(74) *Attorney, Agent, or Firm* — Cozen O'Connor

(57) ABSTRACT

A sensor device includes: a housing body delimiting within the housing body: a flow duct, and a bypass that branches off from the flow duct at a branching point, the bypass having a wall with an opening; and a sensor element configured to detect a gas content, the sensor element being arranged in the opening. The sensor element has: a sensor body having a longitudinal axis, an electrode chamber within the sensor body, a heating element embedded in the sensor body and by which a predefined region around the electrode chamber is heatable to a predefined operating temperature, an inlet duct coupled to the electrode chamber and having an inlet on the surface of the sensor body, and a thermal insulation sleeve on the sensor body, the thermal insulation sleeve extending at least axially in the direction of the longitudinal axis over a region of the electrode chamber.

11 Claims, 3 Drawing Sheets

(56) References Cited

U.S. PATENT DOCUMENTS

| | | | |
|---|---|---|---|
| 7,493,796 B2 | 2/2009 | Wilde | |
| 2001/0054309 A1* | 12/2001 | Ohmori | F01N 13/008 |
| | | | 73/114.73 |
| 2007/0144250 A1* | 6/2007 | Ramsesh | G01F 25/0053 |
| | | | 73/204.22 |
| 2011/0011152 A1 | 1/2011 | Ito et al. | |
| 2011/0186431 A1* | 8/2011 | Horisaka | G01N 27/4075 |
| | | | 204/424 |
| 2014/0130572 A1* | 5/2014 | Otsuka | G01M 15/102 |
| | | | 73/23.31 |
| 2014/0174165 A1* | 6/2014 | Magera | G01M 15/04 |
| | | | 73/114.31 |

FOREIGN PATENT DOCUMENTS

| | | |
|---|---|---|
| DE | 100 52 005 | 5/2002 |
| DE | 10 2004 002 711 | 8/2004 |
| DE | 10 2004 054 014 | 5/2006 |
| DE | 10 2007 030 795 | 1/2008 |
| DE | 10 2007 035 035 | 2/2008 |
| DE | 10 2007 042975 A1 | 3/2009 |
| WO | WO 2005/090959 A1 | 9/2005 |

\* cited by examiner

SENSOR DEVICE

CROSS-REFERENCE TO RELATED APPLICATIONS

This is a U.S. national stage of application No. PCT/EP2014/055531, filed on 19 Mar. 2014, which claims priority to the German Application No. DE 10 2013 204 911.0 filed 20 Mar. 2013, the content of both incorporated herein by reference.

BACKGROUND OF THE INVENTION

1. Field of the Invention

The invention relates to a sensor device that includes a sensor element for detecting a gas content in an environment of the sensor device.

2. Related Art

Gas sensors, in particular oxygen sensors, are used in the intake tract or in the exhaust tract of internal combustion engines, for example gasoline or diesel engines. Such oxygen sensors are, for example, linear lambda sensors. Such lambda sensors predominantly have a sensor element that must be heated to approximately 800° C.

For exhaust-gas sensors, use is made of housings suitable for high temperatures. Such exhaust-gas sensors have a protective cap system which, aside from providing mechanical protection, also performs, inter alia, the following tasks:

ensuring a gas exchange at the gas inlet of the measurement element, protecting against cooling in the case of high gap flow rates, protecting against water droplets, and protecting against water hammer.

SUMMARY OF THE INVENTION

An object of the present invention is to provide a sensor device, in particular for an intake tract of an internal combustion engine, which sensor device permits simple and inexpensive production of the sensor device.

According to one aspect of the invention, a sensor device is provided that includes a housing body having a flow duct formed in the housing body. The sensor device has a bypass formed in the housing body that branches off from the flow duct at a branching point. The bypass has a wall with an opening. The sensor device includes a sensor element for detecting a gas content in an environment of the sensor element, which sensor element is at least partially arranged in the opening in the wall of the bypass. The sensor element is configured to detect a gas content in an environment of the sensor element. The sensor element has a sensor body. The sensor element furthermore has an electrode chamber formed in the sensor body. The sensor element has a heating element embedded in the sensor body and by which a predefined region around the electrode chamber can be heated to a predefined operating temperature. The sensor element has a longitudinal axis and an inlet duct which is coupled to the electrode chamber and which has an inlet on the surface of the sensor body. Further, the sensor element has a thermal insulation sleeve on the sensor body, which thermal insulation sleeve extends at least axially in the direction of the longitudinal axis over the region of the electrode chamber.

The sensor device is preferably arranged in an intake tract of an internal combustion engine. The duct structure with flow duct and bypass advantageously makes it possible for a small gas quantity to be coupled out of a main gas flow in the intake tract and conducted past the sensor element. The flow speed prevailing in the bypass and at the sensor element is a function of the flow speed of the main gas flow. The duct structure makes it possible for a gas exchange to be ensured at all times.

The housing body permits effective protection of the sensor element. The sensor device with the duct structure permits a rapid response of the sensor element. The housing body may be of elongate and thus inexpensive form. A circular form of the housing body is not necessary.

By the thermal insulation in the region of the electrode chamber, the sensor element exhibits very good thermal shock resistance, without this altering the measurement speed. Furthermore, owing to the insulation, heat transport by convection is largely eliminated. In this way, a greater flow can be accepted at the sensor element, whereby the response speed of the sensor element can be improved.

The predefined operating temperature is, for example, a temperature in the range between 600° C. and 850° C.

In an advantageous refinement, the sensor element has a face surface, running substantially perpendicular to the longitudinal axis, of the sensor body, the face surface of the sensor body having the inlet and being arranged in the bypass. In particular, the sensor element is arranged such that the face surface and the wall around the opening run in planar fashion, such that turbulence can be avoided.

In a further advantageous refinement, the bypass is of U-shaped form. This permits simple production of the bypass.

In a further advantageous refinement, the bypass is of omega-shaped form. An omega-shaped form advantageously permits simple production and makes it possible for a flow profile in the bypass to be optimized. Omega-shaped approximately corresponds to horseshoe-shaped.

In a further advantageous refinement, the bypass has at least one flow element that is arranged and configured to at least reduce turbulence in the bypass. This has the advantage that falsification of measurement results owing to turbulence in the bypass can be substantially prevented.

In a further advantageous refinement, the bypass has at least one cavity for the discharge of foreign particles out of the bypass. It is advantageously thus possible for water particles to be discharged out of the bypass.

In a further advantageous refinement, the face surface is free from the insulation sleeve, and the insulation sleeve is spaced apart from the face surface to a predefined extent. The face surface is, for example, spaced apart to a predefined extent such that the sensor element projects slightly out of the insulation sleeve. In this way, the gas inlet is not affected by the insulation sleeve.

In a further advantageous refinement, the housing body has plastic or is composed of plastic. This permits inexpensive production of the sensor device. The plastic is preferably temperature-resistant up to a maximum temperature of 125° C. to 200° C.

In a further advantageous refinement, the housing body has aluminum or is composed of aluminum. This, too, permits inexpensive production of the sensor device.

In a further advantageous refinement, the sensor device has a pressure sensor element and/or a temperature sensor element. This has the advantage that no further separate pressure sensor device or temperature sensor device is required in the vicinity of the sensor device. For correct determination of the oxygen content, a pressure correction is generally necessary. The provision of the pressure sensor element in the sensor device makes it possible that no further separate pressure sensor device has to be arranged in the vicinity of the sensor device. The sensor device with the housing body makes it possible that the temperature sensor element can be arranged so as to have an adequate spacing to the heated sensor element, and thus a temperature measurement adjacent to the sensor element is possible with adequate reliability.

In a further advantageous refinement, the sensor device has a cooling body coupled in a predefined region to the sensor body, wherein the predefined region is, axially in the direction of the longitudinal axis, arranged outside the region in which the insulation sleeve is arranged. The cooling body preferably has a material with very good thermal conductivity, for example a metal.

In a further advantageous refinement, the insulation sleeve has ceramic fibers and/or metal fibers. Specifically such fibers are resistant to high temperatures and, at the same time, exhibit extremely low thermal conductivity. The insulation sleeve is composed, for example, of a ceramic fiber wool of approximately 2 mm thickness.

In a further advantageous refinement, the ceramic fibers and/or the metal fibers are arranged in a metal sleeve. The metal sleeve is, for example, fixedly welded to the sensor element, whereby an extremely stable insulation sleeve can be realized.

In a further advantageous refinement, the ceramic fibers and/or the metal fibers are spaced apart from the metal sleeve by an air gap. In this way, a further insulation action can be realized by way of the air gap.

BRIEF DESCRIPTION OF THE DRAWINGS

Exemplary embodiments of the invention will be discussed in more detail below on the basis of the schematic drawings, in which.

DETAILED DESCRIPTION OF THE PRESENTLY PREFERRED EMBODIMENTS

Elements of identical design or function are denoted by the same reference signs throughout the figures.

Figure 1:
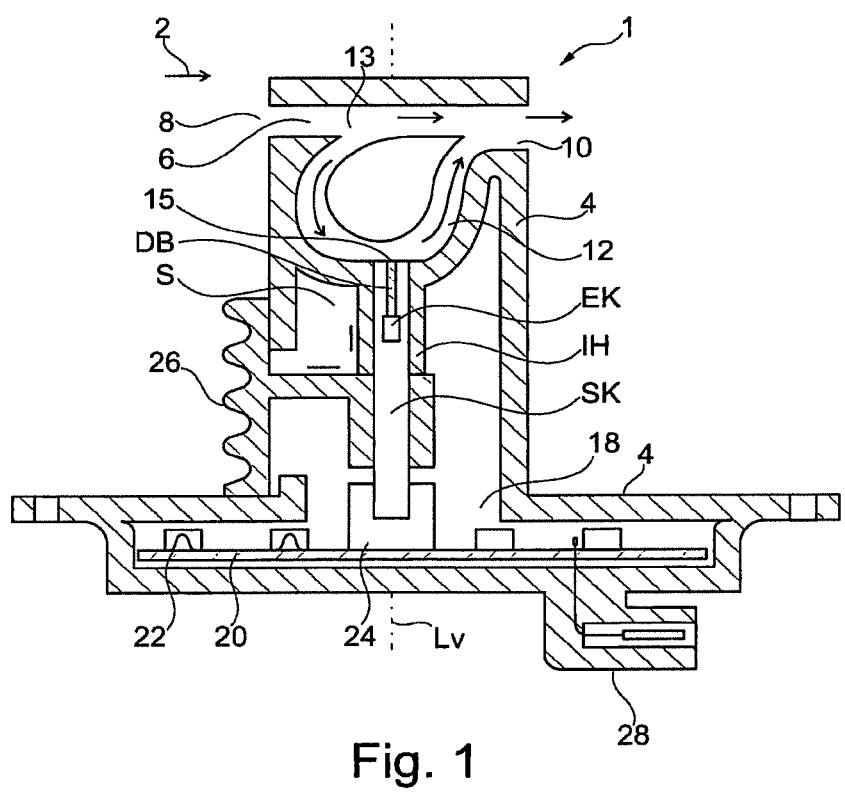
FIG. 1 shows a sensor device for an intake tract.

FIG. 1 shows a sensor device 1 arranged in a main duct. A main gas flow 2 flows in the main duct. The main duct may in particular be an intake line in an internal combustion engine, which is flowed through by an inducted air flow.

The sensor device 1 comprises a housing body 4. In the housing body 4 there is arranged a flow duct 6 with an inlet 8 and an outlet 10. The flow duct 6 may, for example, be of rectilinear form in the housing body 4, and is preferably arranged, by way of an orientation of the housing body 4, such that the inlet 8 of the flow duct faces in the opposite direction in relation to a main flow direction of the air mass flowing past.

The sensor device 1 has a device longitudinal axis Lv. Furthermore, the sensor device 1 has a first end region and a second end region. The flow duct 6 is arranged in the first end region. The sensor device 1 is, for example, installed into the intake line in a suspended configuration, such that, in an installed state, the device longitudinal axis Lv runs substantially perpendicular to the main duct, and the second end region is mechanically connected to a wall of the main duct.

Also arranged in the housing body 4 is a bypass 12, which branches off from the flow duct 6 at a branching point 13.

In FIG. 1, the bypass 12 is, by way of example, of omega-shaped form. The expression "horseshoe-shaped" may also be used instead of "omega-shaped". The bypass 12 may alternatively also be of U-shaped form, for example. The bypass 12 has, for example, at least one flow element arranged and designed to at least reduce turbulence in the bypass 12. Furthermore, the bypass 12 has at least one cavity for the discharge of foreign particles out of the bypass 12.

The bypass 12 has a wall with an opening. A sensor element S for detecting a gas content in an environment of the sensor element S is arranged at least partially in the opening of the wall. An inlet EA (shown, for example, in FIG. 2) of the sensor element S is arranged in the bypass 12. The sensor element S is in particular designed as an oxygen sensor that can detect an oxygen content in the environment of the sensor element S.

Figure 2:
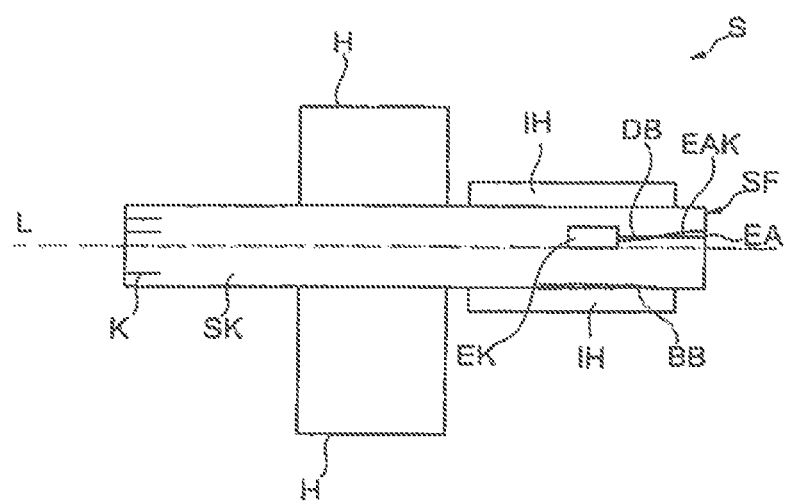
FIG. 2 shows a sensor element for detecting a gas content.

The sensor element S has a sensor body SK, a longitudinal axis, and a face surface SF, shown in FIG. 2, of the sensor body SK, the face surface running substantially perpendicular to the longitudinal axis of the sensor body SK.

The opening in the wall of the bypass 12 is preferably formed in the housing body 4 along the device longitudinal axis Lv of the sensor device 1, such that, proceeding from the face surface SF arranged in the bypass 12, the sensor element S extends along the device longitudinal axis in the direction of the second end region of the sensor device 1.

The construction of the sensor element S is shown in more detail in FIG. 2.

The housing body 4 of the sensor device 1 (FIG. 1) has an electronics chamber 18 which is separated from the flow duct 6 and from the bypass 12. The sensor device 1 has a printed circuit board 20 arranged in or substantially in the electronics chamber 18. Various electronics components 22 are, for example, arranged on the printed circuit board 20.

Furthermore, on the printed circuit board 20, there is arranged a contact element 24 for the mechanical and/or electrical coupling of the sensor element S to the printed circuit board 20. The contact element 24 may, for example, be used for the coupling of lines, which are arranged on or in the sensor body SK of the sensor element S, to conductor tracks of the printed circuit board 20. The coupling may be realized for example by way of cables, wirebonds or leadframes.

The housing body 4 is preferably formed in at least two parts. For example, the housing body 4 has a plastic or is composed of a plastic. The plastic is preferably temperature-resistant up to a maximum temperature of 125° C. to 200° C. The plastic comprises polypropylene and/or polyamides, for example.

In addition or alternatively, the housing body may have aluminum.

The flow duct 6 and the bypass 12 are for example arranged in a first housing body which is connectable to a second housing body.

The sensor device 1 has a cooling body 26, which is coupled in a predefined region to the sensor body SK, wherein the predefined region is, axially in the direction of the longitudinal axis, arranged outside the region in which an insulation sleeve IH is arranged. The cooling body 26 is, for example, designed so as to couple the sensor body SK to the housing body 4, and thus also has the function of a holder H (See FIG. 2).

The sensor device 1 has, for example, a pressure sensor element and/or a temperature sensor element. The pressure sensor element and/or temperature sensor element are in this case arranged, for example, adjacent to the bypass 12. Since the sensor element S is open only at the face side and, with respect to the device longitudinal axis Lv, is arranged axially in the direction of the second end region proceeding from the opening in the wall of the bypass 12, only minor falsification of the temperature measurement occurs.

Furthermore, the sensor device 1 has a plug connector 28 for the electrical coupling of the sensor device 1 to suitable evaluation units, for example. The plug connector 28 is, for example, coupled in a predefined manner to the printed circuit board 20.

The housing body 4 is, for example, designed such that installation in the intake line at the correct angle can be ensured. Such angularly coded installation of the sensor device 1 makes it possible to ensure, with little outlay, that an adequate gas exchange between the main duct and the sensor device 1 can take place.

FIG. 2 shows the sensor element S for detecting a gas content in an environment of the sensor element S. The sensor element S is in particular designed as an oxygen sensor which can detect an oxygen content in the surroundings of the sensor element S. The sensor element S comprises a sensor body SK. The sensor body SK comprises, for example, a substrate composed of yttrium-stabilized zirconium oxide YSZ. An electrode chamber EK is formed in the sensor body SK. Furthermore, in the sensor body SK, there is embedded a heating element by which a predefined region BB around the electrode chamber EK can be heated to a predefined operating temperature. The predefined operating temperature lies for example between 600° C. and 850° C., or is approximately 700° C.

The sensor body SK has an inlet duct EAK which is coupled to the electrode chamber EK and which has the inlet EA in the surface of the sensor body SK, wherein the inlet EA is formed on the face surface SF of the sensor body SK. The inlet EA provides a gas inlet 15 from the bypass 12 into the electrode chamber EK.

Between the inlet EA and the electrode chamber EK, there is formed a diffusion barrier DB through which oxygen can diffuse into the electrode chamber EK.

Furthermore, the sensor element S has the thermal insulation sleeve IH, which is formed on the sensor body SK and which extends at least axially in the direction of the longitudinal axis L over the region of the electrode chamber EK.

Figure 3:
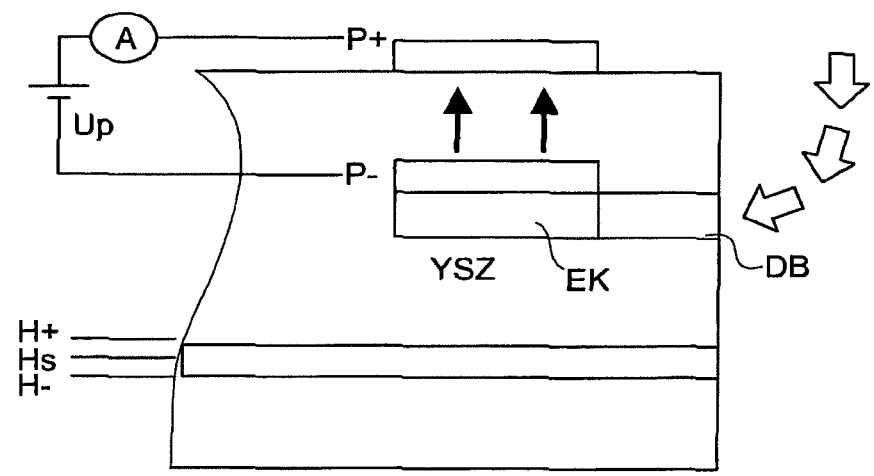
FIG. 3 shows a further view of the sensor element for detecting the gas content.

FIG. 3 shows a second view of the sensor element S. FIG. 3 illustrates the layered construction of the sensor element S. A first electrode P− is connected to the electrode chamber EK, which first electrode can also be referred to as a cathode. Between the first electrode P− and a second electrode P+, which can also be referred to as an anode, there is formed a solid electrolyte layer, which is formed, for example, by way of yttrium-stabilized zirconium oxide YSZ.

The sensor element S furthermore has multiple contacts (see FIG. 2), for example for the actuation of heating elements and for the application of a voltage for the operation of the sensor element S.

Furthermore, the sensor element S has a holder H (see FIG. 2) which may also serve for the dissipation of heat. For this purpose, the holder H is, for example, formed from aluminum, and is fastened to the sensor body SK for example by adhesive.

The functioning of the sensor element S will be described below.

To detect the gas content of the environment of the sensor element S, a voltage difference of, for example, 0.8 V is applied between the first electrode P− and the second electrode p+. If the oxygen content under the cathode is set to 0 and the sensor element S is introduced into an environment containing oxygen, it is the case, owing to the concentration difference or the partial pressure difference between the environment and the region under the cathode, in which virtually no oxygen is present, that oxygen atoms diffuse through the diffusion barrier DB and the cathode into the substrate of the sensor body SK. The oxygen atoms diffuse, as double negatively charged ions, into the substrate of the sensor body SK, wherein the electrons required for the ionization of the oxygen atoms are provided by the electrically conductive cathode. If a voltage is applied between the electrodes, the difference diffusion limiting current is measured. The current is dependent, in the case of an oxygen-containing measurement gas, on the oxygen partial pressure. At the anode, the oxygen ions are converted into oxygen atoms again, which diffuse through the anode again into the oxygen-containing environment. For adequate ion conductivity, the sensor body SK must be at an elevated temperature. Therefore, the sensor body SK is heated by the heating element, in the heatable region BB of the electrode chamber EK, to a predefined operating temperature of for example between 600° C. and 850° C.

For protection against thermal shock, the sensor element S has the insulation sleeve IH. By the thermal insulation in the region of the electrode chamber EK, the sensor element S exhibits very good thermal shock resistance, without this altering the measurement speed. Furthermore, owing to the insulation, the heat transport by convection is largely eliminated. In this way, a greater flow can be accepted at the sensor element S, whereby the response speed of the sensor element S can be improved.

The insulation sleeve IH has, for example, ceramic fibers and/or metal fibers. The ceramic fibers and/or metal fibers are, for example, arranged in a metal sleeve. Alternatively or in addition, the ceramic fibers and/or metal fibers are spaced apart from the metal sleeve by an air gap. The insulation sleeve IH has, for example, a thickness of approximately 2 mm.

The face surface SF of the sensor element S is, for example, free from the insulation sleeve IH, and the insulation sleeve IH is spaced apart from the face surface SF to a predefined extent. The face surface SF is for example spaced apart to a predefined extent such that the sensor element S projects slightly out of the insulation sleeve IH. In this way, the inlet EA is not affected by the insulation sleeve IH, whereby the measurement is not influenced.

Thus, while there have been shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A sensor device (1), comprising:
a housing body (4), the housing body (4) delimiting within the housing body (4):
   a flow duct (6), and
   a bypass (12) that branches off from the flow duct (6) at a branching point (13), the bypass (12) having a wall with an opening; and
   a sensor element (S) configured to detect a gas content in an environment of the sensor element (S), the sensor element being at least partially arranged in the opening in the wall of the bypass (12), the sensor element (S) having:
      a sensor body (SK) having a longitudinal axis (L),
      an electrode chamber (EK) within the sensor body (SK),
      a heating element embedded in the sensor body (SK) and by which a predefined region (BB) around the electrode chamber (EK) is heatable to a predefined operating temperature,
      an inlet duct (EAK) coupled to the electrode chamber (EK) and having an inlet (EA) on the surface of the sensor body (SK), and
      a thermal insulation sleeve (IH) on and radially contacting the sensor body (SK), the thermal insulation sleeve extending at least axially in the direction of the longitudinal axis (L) over a region of the electrode chamber (EK),
   wherein the sensor element (S) has a face surface (SF), running substantially perpendicular to the longitudinal axis (L), of the sensor body (SK), wherein the face surface (SF) of the sensor body (SK) has the inlet (EA) and is arranged in the bypass (12), and
   wherein the face surface (SF) is free from the insulation sleeve (IH) and the insulation sleeve (IH) is longitudinally spaced apart from the face surface (SF) such that the sensor element (S) at the face surface (SF) projects out of the insulation sleeve (IH).

2. The sensor device (1) as claimed in claim 1, wherein the bypass (12) is of an omega-shaped form.

3. The sensor device (1) as claimed in claim 1, wherein the bypass (12) has at least one flow element arranged and configured to at least reduce turbulence in the bypass (12).

4. The sensor device (1) as claimed in claim 1, wherein the bypass (12) has at least one cavity for the discharge of foreign particles out of the bypass (12).

5. The sensor device (1) as claimed in claim 1, wherein the housing body (4) has a plastic or is composed of plastic.

6. The sensor device (1) as claimed in claim 1, wherein the housing body (4) has aluminum or is composed of aluminum.

7. The sensor device (1) as claimed in claim 1, further comprising at least one selected from the group of: a pressure sensor element and a temperature sensor element.

8. The sensor device (1) as claimed in claim 1, further comprising a cooling body (26) coupled, in a predefined region, to the sensor body (SK), wherein the predefined region is, axially in the direction of the longitudinal axis (L), arranged outside the region in which the insulation sleeve (IH) is arranged.

9. The sensor device (1) as claimed in claim 1, wherein the insulation sleeve (IH) has ceramic fibers and/or metal fibers.

10. The sensor device (1) as claimed in claim 9, wherein the ceramic fibers and/or metal fibers are arranged in a metal sleeve.

11. The sensor device (1) as claimed in claim 10, wherein the ceramic fibers and/or metal fibers are spaced apart from the metal sleeve by an air gap.

\* \* \* \* \*